United States Patent [19]

Schallner et al.

[11] Patent Number: 4,772,312
[45] Date of Patent: Sep. 20, 1988

[54] 5-AMINO-1-PYRIDYL-PYRAZOLES, COMPOSITION CONTAINING THEM, AND HERBICIDAL METHOD OF USING THEM

[75] Inventors: Otto Schallner, Monheim; Reinhold Gehring, Wuppertal; Jörg Stetter, Wuppertal; Hans-Joachim Santel, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 866,638

[22] Filed: May 22, 1986

[30] Foreign Application Priority Data

Jun. 7, 1985 [DE] Fed. Rep. of Germany ....... 3520330

[51] Int. Cl.⁴ .................... A01N 43/56; C07D 401/04
[52] U.S. Cl. .......................................... 71/92; 546/2; 546/279
[58] Field of Search .................... 546/279, 2; 71/92

[56] References Cited

U.S. PATENT DOCUMENTS 4,620,865 11/1986 Beck et al. .................. 546/279
4,622,330 11/1986 Bochis et al. ................ 548/376

FOREIGN PATENT DOCUMENTS 0034945 9/1981 European Pat. Off. ........ 71/92
0151867 8/1985 European Pat. Off. ....... 546/279
3129429 2/1983 Fed. Rep. of Germany ... 71/92
893755 4/1962 United Kingdom ........... 548/362
2136427 9/1984 United Kingdom ............ 71/92

OTHER PUBLICATIONS

Chemical Abstracts, 94, 192215j (1981).
Chemical Abstracts, 69, 59155g (1968).

Primary Examiner—Mary C. Lee
Assistant Examiner—Kurt G. Briscoe
Attorney, Agent, or Firm—Sprung Horn Kramer & Woods

[57] ABSTRACT

Herbicidally active novel 5-amino-1-pyridyl-pyrazoles of the formula

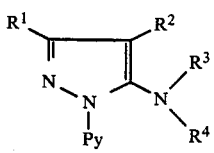

in which
$R^1$ represents hydrogen or represents alkyl with 1 to 12 carbon atoms,
$R^2$ represents hydrogen, nitro, nitroso or halogen, or represents a radical

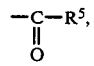

wherein
$R^5$ represents hydrogen, hydroxyl, alkyl, alkenyl, alkinyl, halogenoalkyl, alkoxyalkyl or alkylthioalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
$R^3$ represents hydrogen, or represents a radical

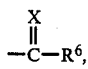

or represents a radical $-S(O)_n-R^7$, $R^4$ represents hydrogen, or represents alkyl, or represents a radical

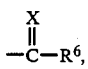

or represents a radical $-S(O)_n-R^7$, and, in the case where $R^3$ represents an $-SO_2-R^7$ radical, also represents an inorganic or organic cation bonded in salt form, and
$R^6$ represents hydrogen, alkyl, alkenyl, alkinyl, halogenoalkyl, alkoxyalkyl or alkylthioalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
X represents oxygen or sulphur,
n represents the number 0, 1 or 2,
$R^7$ represents alkyl, halogenoalkyl or optionally substituted aryl and
Py represents substituted C-linked pyridyl.

Some of the intermediates wherein the 5-position of the pyrazole carries a halogen atom are also new.

9 Claims, No Drawings

5-AMINO-1-PYRIDYL-PYRAZOLES, COMPOSITION CONTAINING THEM, AND HERBICIDAL METHOD OF USING THEM

The invention relates to new 5-amino-1-pyridyl-pyrazoles, several processes for their preparation and their use as herbicides.

It is already known that certain 5-amino-1-aryl-pyrazoles, such as, for example, 4-cyano-5-propionamido-1-(2,3,4-trichlorophenyl)-pyrazole, have herbicidal properties, and in particular also selective herbicidal properties (compare, for example, DE-OS (German Published Specification) No. 3,226,513).

However, their herbicidal action against harmful plants, like their tolerance towards important crop plants, is not always completely satisfactory in all fields of use.

New 5-amino-1-pyridyl-pyrazoles of the general formula (I)

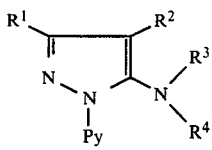
(I)

in which
$R^1$ represents hydrogen or represents alkyl with 1 to 12 carbon atoms,
$R^2$ represents hydrogen, nitro, nitroso or halogen, or represents a radical

wherein
$R^5$ represents hydrogen, hydroxyl, alkyl, alkenyl, alkinyl, halogenoalkyl, alkoxyalkyl or alkylthioalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
$R^3$ represents hydrogen, or represents a radical

or represents a radical $-S(O)_n-R^7$,
$R^4$ represents hydrogen, or represents alkyl, or represents a radical

or represents a radical $-S(O)_n-R^7$, or, in the case where $R^3$ represents a $-SO_2-R^7$ radical, also represents an inorganic or organic cation bonded in salt form,
$R^6$ represents hydrogen, alkyl, alkenyl, alkinyl, halogenoalkyl, alkoxyalkyl or alkylthioalkyl, or represents optionally substituted cyloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
X represents oxygen or sulphur,
n represents the number 0, 1 or 2,
$R^7$ represents alkyl, halogenoalkyl or optionally substituted aryl and
Py represents substituted C-linked pyridyl,
have been found.

It has furthermore been found that the new 5-amino-1-pyridyl-pyrazoles of the general formula (I)

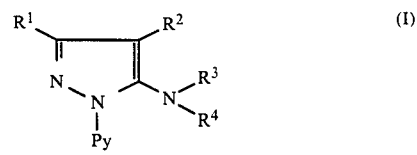
(I)

in which
$R^1$ represents hydrogen or represents alkyl with 1 to 12 carbon atoms,
$R^2$ represents hydrogen, nitro, nitroso or halogen, or represents the radical

wherein
$R^5$ represents hydrogen, hydroxyl, alkyl, alkenyl, alkinyl, halogenoalkyl, alkoxyalkyl or alkylthioalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
$R^3$ represents hydrogen, or represents a radical

or represents a radical $-S(O)_n-R^7$,
$R^4$ represents hydrogen, or represents alkyl, or represents a radical

or represents a radical $-S(O)_n-R^7$, or, in the case where $R^3$ represents an $-SO_2-R^7$ radical, also represents an inorganic or organic cation bonded in salt form,
$R^6$ represents hydrogen, alkyl, alkenyl, alkinyl, halogenoalkyl, alkoxyalkyl or alkylthioalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
X represents oxygen or sulphur,
n represents the number 0, 1 or 2, R[7] represents alkyl, halogenoalkyl or optionally substituted aryl and Py represents substituted C-linked pyridyl, can be prepared by the following processes:

(a) the 5-amino-1-pyridyl-pyrazole derivatives of the formula (Ia) according to the invention

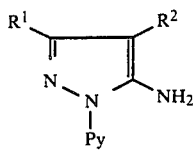
(Ia)

in which

R[1], R[2] and Py have the abovementioned meaning, are obtained by a process in which pyridylhydrazines of the formula (II)

Py—NH—NH$_2$        (II)

in which

Py has the abovementioned meaning, are initially reacted, in a 1st stage, with acrylonitrile derivatives of the formula (III)

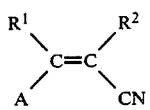
(III)

in which

R[1] and R[2] have the abovementioned meaning and

A represents halogen, hydroxyl, alkoxy or dialkylamino, if appropriate in the presence of a diluent and if appropriate in the presence of a reaction auxiliary, to give the pyridylhydrazine derivatives of the formula (IV)

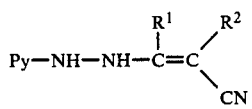
(IV)

in which

R[1], R[2] and Py have the abovementioned meaning, and these are cyclized in a 2nd stage, if appropriate the presence of a diluent and if appropriate in the presence of an acid-binding agent, or (b) the 5-amino-1-pyridyl-pyrazole derivatives of the formula (Ib) according to the invention

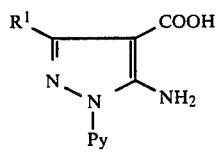
(Ib)

in which

R[1] and Py have the abovementioned meaning, are obtained by a process in which 4-alkoxycarbonyl-5-amino-pyrazoles of the formula (Ir)

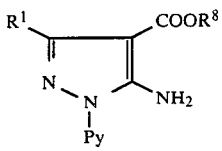
(Ir)

in which

R[1], R[8] and Py have the abovementioned meaning, are hydrolyzed on the ester group in the 4-position of the pyrazole ring in the generally customary manner, if appropriate in the presence of a diluent and if appropriate in the presence of a catalyst, or (c) the 5-amino-1-pyridyl-pyrazole derivatives of the formula (Ic) according to the invention

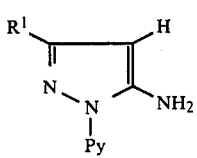
(Ic)

in which

R[1] and Py have the abovementioned meaning, are obtained by a process in which 5-amino-1-pyridylpyrazole derivatives of the formula (Ib)

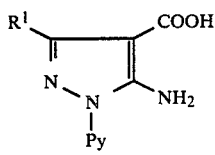
(Ib)

in which

R[1] and Py have the abovementioned meaning, are decarboxylated in the generally customary manner, if appropriate in the presence of a diluent and if appropriate in the presence of a catalyst, or (d) the 5-amino-1-pyridyl-pyrazole derivatives of the formula (Id) according to the invention

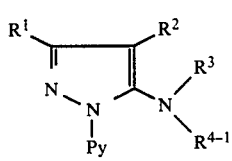
(Id)

in which

R[4-1] represents alkyl, or represents a radical

or represents a radical —S(O)$_n$—R[7] and

R[1], R[2], R[3], R[6], R[7], X and n have the above-mentioned meaning, are obtained by a process in which 5-amino-1-pyridyl-pyrazoles of the formula (Is)

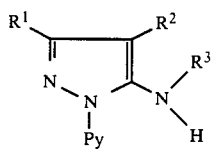 (Is)

in which
R¹, R², R³ and Py have the abovementioned meaning,
are reacted
(d-α) with compounds of the formula (V)

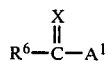 (V)

in which
A¹ represents halogen, or represents a radical

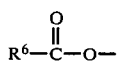

and
R⁶ and X have the abovementioned meaning,
or
(d-β) with compounds of the formula (Va)

$R^7-S(O)_n-A^2$ (Va)

in which
A² represents halogen and
R⁷ and n have the abovementioned meaning,
or
(d-γ) with compounds of the formula (Vb)

$R^8-A^3$ (Vb)

in which
R⁸ represents alkyl and
A³ represents halogen, p-toluenesulphonyloxy or alkoxysulphonyloxy,
if appropriate in the presence of a diluent and if appropriate in the presence of an acid-binding agent, or
(e) the 5-amino-1-pyridyl-pyrazole derivatives of the formula (Ie) according to the invention

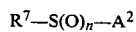 (Ie)

in which
R²⁻¹ represents halogen, nitro, nitroso, formyl, alkanoyl or aroyl and
R¹, R³, R⁴ and Py have the abovementioned meaning,
are obtained by a process in which 5-amino-1-pyridyl-pyrazole derivatives of the formula (It)

 (It)

in which
R¹, R³, R⁴ and Py have the abovementioned meaning,
are substituted in the 4-position with electrophilic agents of the formula (VI)

$R^{2-1}-A^4$ (VI)

in which
A⁴ represents an electron-withdrawing leaving group and
R²⁻¹ has the abovementioned meaning,
or with other customary electrophilic agent, if appropriate in the presence of a diluent and if appropriate in the presence of a catalyst or reaction auxiliary, or
(f) the 5-amino-1-pyridyl-pyrazole derivatives of the formula (If) according to the invention

 (If)

in which
R²⁻² represents halogen, nitro and nitroso,
R⁴⁻² represents hydrogen or alkyl and
R¹ and Py have the abovementioned meaning,
are obtained by a process in which 5-acylamino-1-pyridyl-pyrazoles of the formula (Iu)

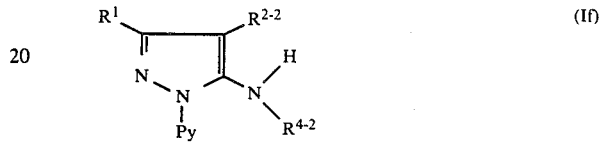 (Iu)

in which
R¹, R²⁻², R⁴⁻², R⁶ and Py have the above-mentioned meaning,
are deacylated on the amino group in the 5-position of the pyrazole ring, if appropriate in the presence of a diluent and if appropriate in the presence of a catalyst, or
(g) the 5-amino-1-pyridyl-pyrazole derivatives of the formula (Ig) according to the invention

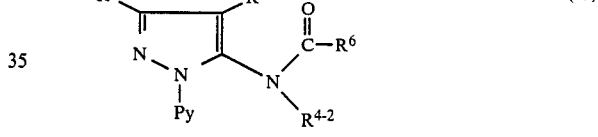 (Ig)

in which
R¹, R⁷ and Py have the abovementioned meaning,
are obtained by a process in which 5-bis-sulphonylaminopyrazoles of the formula (Iv)

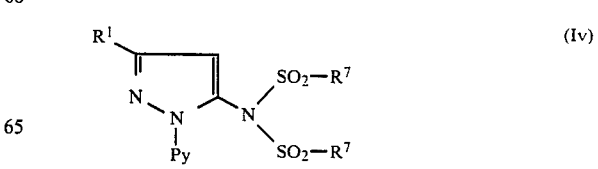 (Iv)

in which $R^1$, $R^7$ and Py have the abovementioned meaning,
are split with bases, if appropriate in the presence of a diluent, or (h) the 5-amino-1-pyridyl-pyrazole derivatives of the formula (Ih) according to the invention

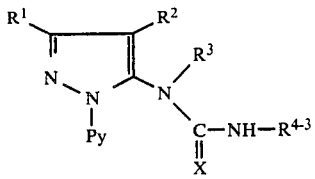
(Ih)

in which
$R^{4\text{-}3}$ represents alkyl, or represents optionally substituted aryl and
$R^1$, $R^2$, $R^3$, X and Py have the abovementioned meaning,
are obtained by a process in which 5-amino-1-pyridyl-pyrazoles of the formula (Is)

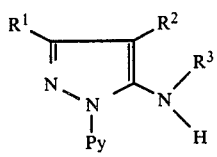
(Is)

in which
$R^1$, $R^2$, $R^3$ and Py have the abovementioned meaning,
are reacted with iso(thio)cyanates of the formula (VII)

$R^{4\text{-}3}\text{—}N\text{=}C\text{=}X$ (VII)

in which
$R^{4\text{-}3}$ and X have the abovementioned meaning,
if appropriate in the presence of a diluent and if appropriate in the presence of an acid-binding agent, or (i) the 5-amino-1-pyridyl-pyrazole derivatives of the formula (Ii) according to the invention

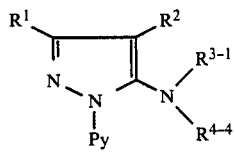
(Ii)

in which
$R^{4\text{-}4}$ represents alkyl,
$R^{3\text{-}1}$ represents hydrogen or alkyl and
$R^1$, $R^2$ and Py have the abovementioned meaning,
are obtained by a process in which 5-halogeno-pyrazoles of the formula (VIII)

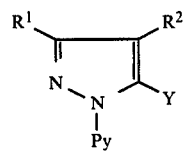
(VIII)

in which
Y represents halogen and
$R^1$, $R^2$ and Py have the abovementioned meaning,
are reacted with amines of the formula (IX)

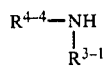
$R^{4\text{-}4}\text{—}NH$
$\quad\quad |$
$\quad\quad R^{3\text{-}1}$
(IX)

in which
$R^{4\text{-}4}$ represents alkyl and
$R^{3\text{-}1}$ represents hydrogen or alkyl,
if appropriate in the presence of a diluent and if appropriate in the presence of an acid-binding agent, or (k) the 5-amino-1-pyridyl-pyrazole derivatives of the formula (Ik) according to the invention

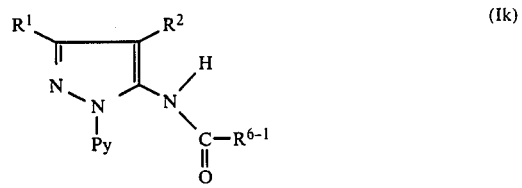
(Ik)

in which
$R^{6\text{-}1}$ represents alkoxy or alkylthio, or represents optionally substituted aryloxy, or represents optionally substituted arylthio, or represents alkylamino or dialkylamino, or represents optionally substituted arylamino and
$R^1$, $R^2$ and Py have the abovementioned meaning,
are obtained by a process in which (bis)carbamates of the formula (Iw)

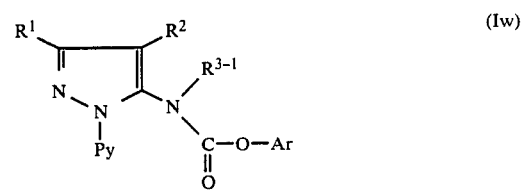
(Iw)

in which
$R^{3\text{-}1}$ represents hydrogen, or represents a radical

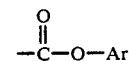
$\quad\quad O$
$\quad\quad \|$
$-C\text{—}O\text{—}Ar$ wherein
Ar represents optionally substituted aryl and
$R^1$, $R^2$ and Py have the abovementioned meaning,
are reacted with compounds of the formula (X)

$R^{6\text{-}1}\text{—}H$ (X)

in which
$R^{6\text{-}1}$ has the abovementioned meaning,
if appropriate in the presence of a diluent and if appropriate in the presence of a basic catalyst, or (l) salts of 5-sulphonamido-pyrazole derivatives of the formula (Ix) according to the invention are obtained by a process in which a salt is formed on the nitrogen of the sulphonamide group of 5-sulphonamide-pyrazoles of the formula (Ix)

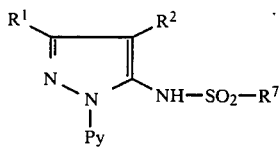 (Ix)

in which
R¹, R², R⁷ and Py have the abovementioned meaning,
by reaction either with salts of the formula (XI)

$$M^{\oplus} - G^{\ominus}$$ (XI)

in which
M⊕ represents one equivalent of an inorganic or organic cation and
G⊖ represents one equivalent of a suitable counter-ion,
or with primary, secondary or tertiary amines, if appropriate in the presence of a diluent.

Finally, it has been found that the new 5-amino-1-pyridyl-pyrazoles of the general formula (I) have herbicidal properties, and in particular also selective herbicidal properties.

Surprisingly, the 5-amino-1-pyridyl-pyrazoles of the general formula (I) according to the invention, in addition to having a clearly improved general herbicidal activity against harmful plants, also exhibit a considerably improved tolerance towards important crop plants in comparison with the 5-amino-1-aryl-pyrazoles known from the prior art, such as, for example, 4-cyano-5-propionamido-1-(2,3,4-trichlorophenyl)-pyrazole, which are closely related compounds chemically and from the point of view of their action.

Formula (I) provides a general definition of the 5-amino-1-pyridyl-pyrazoles according to the invention. Preferred compounds of the formula (I) are those in which
R¹ represents hydrogen, or represents straight-chain or branched alkyl with 1 to 8 carbon atoms,
R² represents hydrogen, nitro, nitroso, fluorine, chlorine, bromine or iodine, or represents a radical

wherein
R⁵ represents hydrogen, hydroxyl or straight-chain or branched alkyl with 1 to 12 carbon atoms, or represents in each case straight-chain or branched alkenyl, alkinyl, alkoxyalkyl, alkylthioalkyl, alkoxy, alkylthio, alkylamino, dialkylamino or halogenoalkyl with in each case up to 4 carbon atoms in the individual alkyl parts and, in the case of halogenoalkyl, with up to 9 identical or different halogen atoms, or furthermore represents cycloalkyl which has 3 to 7 carbon atoms and is optionally monosubstituted or polysubstituted by identical or different substituents from the group comprising halogen, C₁-C₄-alkyl and C₁-C₄-halogenoalkyl, or represents phenyl, phenoxy, phenylthio or phenylamino, in each case optionally monosubstituted or polysubstituted by identical or different substituents, possible phenyl substituents in each case being: halogen and in each case straight-chain or branched alkyl and alkoxy with in each case 1 to 4 carbon atoms and halogenoalkyl with 1 to 4 carbon atoms and 1 to 9 identical or different halogen atoms, R³ represents hydrogen, or represents a radical

or represents a radical —S(O)ₙ—R⁷,
R⁴ represents hydrogen, or represents a radical

or represents a radical —S(O)ₙ—R⁷, or represents straight-chain or branched alkyl with 1 to 6 carbon atoms, or, in the case where R³ represents a radical —SO₂—R⁷, also represents one equivalent of an alkali, alkaline earth or transition metal cation bonded in salt form, or represents an optionally by C₁-C₄-alkyl or phenyl substituted ammonium ion,
wherein
R⁶ represents hydrogen, or represents straight-chain or branched alkyl with 1 to 12 carbon atoms, or represents in each case straight-chain or branched alkenyl or alkinyl with in each case 2 to 4 carbon atoms, or represents in each case straight-chain or branched alkoxyalkyl, alkylthioalkyl, alkoxy, alkylthio, alkylamino, dialkylamino or halogenoalkyl with in each case 1 to 4 carbon atoms in the individual alkyl parts and, in the case of halogenoalkyl, with up to 9 identical or different halogen atoms, furthermore represents cycloalkyl which has 3 to 7 carbon atoms and is optionally monosubstituted or polysubstituted by identical or different substituents from the group comprising halogen, C₁-C₄-alkyl and C₁-C₄-halogenoalkyl, or represents phenyl, phenoxy, phenylthio or phenylamino, in each case optionally monosubstituted or polysubstituted by identical or different substituents, possible phenyl substituents in each case being: halogen and in each case straight-chain or branched alkyl and alkoxy with in each case 1 to 4 carbon atoms and halogenoalkyl with 1 to 4 carbon atoms and 1 to 9 identical or different halogen atoms,
R⁷ represents in each case straight-chain or branched alkyl or halogenoalkyl with in each case 1 to 4 carbon atoms and, where appropriate, 1 to 9 identical or different halogen atoms, or represents phenyl which is optionally monosubstituted or polysubstituted by identical or different substituents, possible phenyl substituents being: halogen and in each case straight-chain or branched alkyl and alkoxy with in each case 1 to 4 carbon atoms and halogenoalkyl with 1 to 4 carbon atoms and 1 to 9 identical or different halogen atoms,
X represents oxygen or sulphur,
n represents the number 0, 1 or 2 and
Py represents 2-pyridyl, 3-pyridyl or 4-pyridyl, in each case monosubstituted or polysubstituted by identical or different substituents, possible substituents being: cyano, nitro, halogen, in each case straight-chain or branched alkyl, alkoxy and alkoxycarbonyl with in each case 1 to 4 carbon atoms in the alkyl part, in each case straight-chain or branched halogenoalkyl and halogenoalkoxy with in each case 1 to 4 carbon atoms and 1 to 9 identical or different halogen atoms and a radical —S(O)$_m$—R$^9$, wherein R$^9$ represents amino, or represents in each case straight-chain or branched alkyl, alkylamino or dialkylamino with in each case 1 to 4 carbon atoms in the individual alkyl parts, or represents halogenoalkyl with 1 to 4 carbon atoms and with 1 to 9 identical or different halogen atoms and m represents the number 0, 1 or 2.

Particularly preferred compounds of the formula (I) in which

R$^1$ represents hydrogen, methyl, ethyl, n- or i-propyl or n-, i-, s- or t-butyl, R$^2$ represents hydrogen, nitro, nitroso, fluorine, chlorine, bromine or iodine, or represents a radical

wherein

R$^5$ represents hydrogen, hydroxyl, methyl, ethyl, n- or i-propyl, n-, i-, s- or t-butyl, n- or i-pentyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 2-chloropropyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl and trifluoromethyl, or represents phenyl, phenoxy, phenylthio or phenylamino, in each case optionally mono-, di- or trisubstituted by identical or different substituents from the group comprising methyl, methoxy, chlorine and trifluoromethyl, R$^3$ represents hydrogen, or represents a radical

or represents a radical —S(O)$_n$—R$^7$,

R$^4$ represents hydrogen, or represents a radical

or represents a radical —S(O)$_n$—R$^7$, or represents methyl, ethyl, n- or i-propyl or n-, i-, s- or t-butyl, or, in the case where R$^3$ represents a radical —SO$_2$—R$^7$, also represents one equivalent of a sodium, potassium, magnesium, calcium, barium, copper, zinc, manganese, tin, iron, cobalt or nickel ion bonded in salt form, or represents an ammonium ion which is optionally mono-, di- or trisubstituted by identical or different substituents from the group comprising methyl, ethyl, n- and i-propyl, n-, i-, s- and t-butyl and phenyl, wherein R$^6$ represents hydrogen, methyl, ethyl, n- or i-propyl, n-, i-, s- or t-butyl, n- or i-pentyl, n- or i-hexyl, n- or i-heptyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 3-chloropropyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl and trifluoromethyl, or represents phenyl, phenoxy, phenylthio or phenylamino, in each case optionally mono-, di- or trisubstituted by identical or different substituents from the group comprising methyl, methoxy, chlorine and trifluoromethyl, R$^7$ represents methyl, ethyl, n- or i-propyl, n-, i, s- or t-butyl, chloromethyl, dichloromethyl, trichloromethyl or trifluoromethyl, or represents phenyl which is optionally mono-, di- or trisubstituted by identical or different substituents from the group comprising methyl, methoxy, chlorine and trifluoromethyl, X represents oxygen or sulphur, n represents the number 0, 1 or 2 and Py represents 2-pyridyl or 4-pyridyl, in each case mono-, di-, tri- or tetrasubstituted by identical or different substituents, possible substituents being: cyano, nitro, fluorine, chlorine, bromine, iodine, methyl, ethyl, n- and i-propyl, n-, i-, S- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)$_m$—R$^9$, wherein R$^9$ represents amino, methylamino, ethylamino, dimethylamino, diethylamino, fluorodichloromethyl, difluoromethyl, tetrafluoroethyl, trifluorochloroethyl, trifluoromethyl, methyl or ethyl and m represents the number 0, 1 or 2.

The following 5-amino-1-pyridyl-pyrazoles of the general formula (I) may be mentioned specifically, in addition to the compounds mentioned in the preparation examples:

TABLE 1
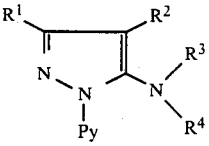
| R¹ | R² | R³ | R⁴ | Py |
|---|---|---|---|---|
| H | NO$_2$ | H | H | 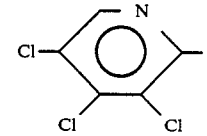 |
| H | NO$_2$ | —CO—C$_2$H$_5$ | H | 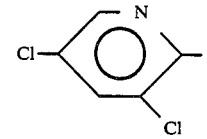 |
| H | Cl | H | H | 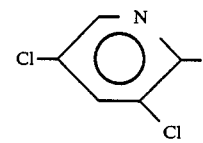 |
| H | Cl | —CO—C$_2$H$_5$ | H | 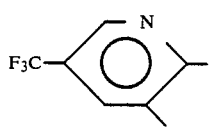 |
| H | NO$_2$ | —CO—C$_2$H$_5$ | CH$_3$ | 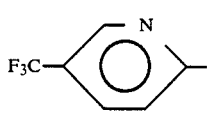 |
| H | NO$_2$ | H | H | 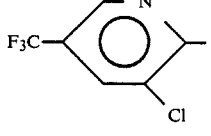 |
| H | NO$_2$ | —CO—C$_2$H$_5$ | H | 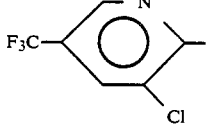 |
| H | —CO—OC$_2$H$_5$ | H | H | 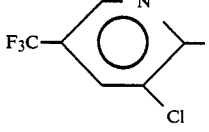 |
| H | —CO—OC$_2$H$_5$ | H | H | 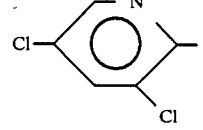 |

TABLE 1-continued

Structure (I): pyrazole with R¹ at 3-position, R² at 4-position, N(R³)(R⁴) at 5-position, and Py group on N1.

| R¹ | R² | R³ | R⁴ | Py |
|---|---|---|---|---|
| H | NO₂ | —CO—CHCl₂ | H | 3,5-dichloropyridin-2-yl |
| H | NO₂ | —CO—CHCl₂ | H | 5-CF₃, 3-Cl pyridin-2-yl |
| H | NO₂ | —C₄H₉—n | H | 5-CF₃, 3-Cl pyridin-2-yl |
| H | NO₂ | H | H | 5-CF₃, 3-Cl pyridin-2-yl |
| CH₃ | NO₂ | H | H | 5-CF₃, 3-Cl pyridin-2-yl |
| H | NO₂ | —CO—OCH₃ | H | 5-CF₃, 3-Cl pyridin-2-yl |
| H | NO₂ | —CO—NH—C₃H₇—i | H | 5-CF₃, 3-Cl pyridin-2-yl |
| H | NO₂ | —CO—O—C₆H₅ | H | 3,5-dichloropyridin-2-yl |
| H | NO₂ | —CO—NH—CH₃ | H | 3,5-dichloropyridin-2-yl |

TABLE 1-continued (I)

[Structure: pyrazole with R¹ at 3-position, R² at 4-position, NR³R⁴ at 5-position, Py on N1]

| R¹ | R² | R³ | R⁴ | Py |
|---|---|---|---|---|
| H | NO₂ | —SO₂—CH₃ | H | 3,5-dichloropyrid-2-yl |
| H | NO₂ | —SO₂—CH₃ | —SO₂—CH₃ | 3,5-dichloropyrid-2-yl |
| H | NO₂ | —CO—C₂H₅ | —C₃H₇—n | 3-chloro-5-trifluoromethylpyrid-2-yl |
| H | NO₂ | H | H | 3,5-dibromopyrid-2-yl |
| H | NO₂ | H | H | 3,5-dibromopyrid-2-yl |
| H | —CO—OC₂H₅ | H | H | 3,5-dibromopyrid-2-yl |
| CH₃ | —CO—OC₂H₅ | H | H | 3-chloro-5-trifluoromethylpyrid-2-yl |
| CH₃ | NO₂ | —CO—C₂H₅ | H | 3-chloro-5-trifluoromethylpyrid-2-yl |

If, for example, N-(3,5-dichloropyrid-2-yl)-hydrazine and ethoxymethylenemalonic acid monoethyl ester-nitrile are used as starting substances, the course of the reaction in process (a) according to the invention can be represented by the following equation:

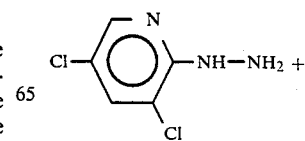

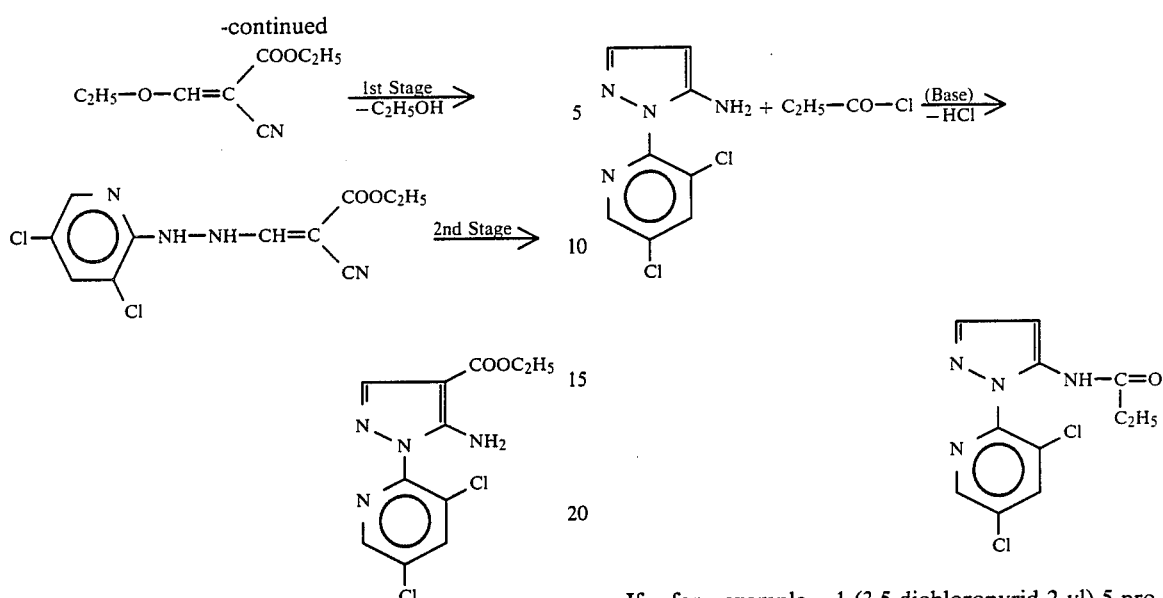

If, for example, 5-amino-1-(3,5-dichloropyrid-2-yl)-4-ethoxycarbonyl-pyrazole is used as the starting substance, the course of the reaction in process (b) according to the invention can be represented by the following equation:

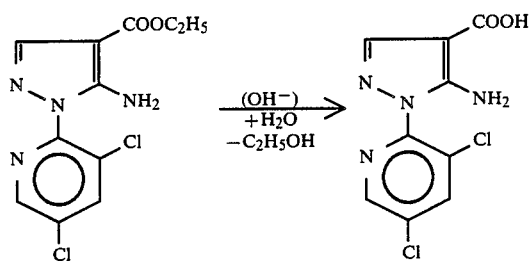

If, for example, 5-amino-1-(3,5-dichloropyrid-2-yl)-pyrazole-4-carboxylic acid is used as the starting substance, the course of the reaction in process (c) according to the invention can be represented by the following equation:

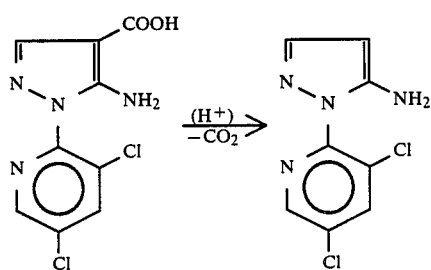

If, for example, 5-amino-1-(3,5-dichloropyrid-2-yl)-pyrazole and propionyl chloride are used as starting substances, the course of the reaction in process (d) according to the invention can be represented by the following equation:

If, for example, 1-(3,5-dichloropyrid-2-yl)-5-propionamido-pyrazole and nitric acid are used as starting substance, the course of the reaction in process (e) according to the invention can be represented by the following equation:

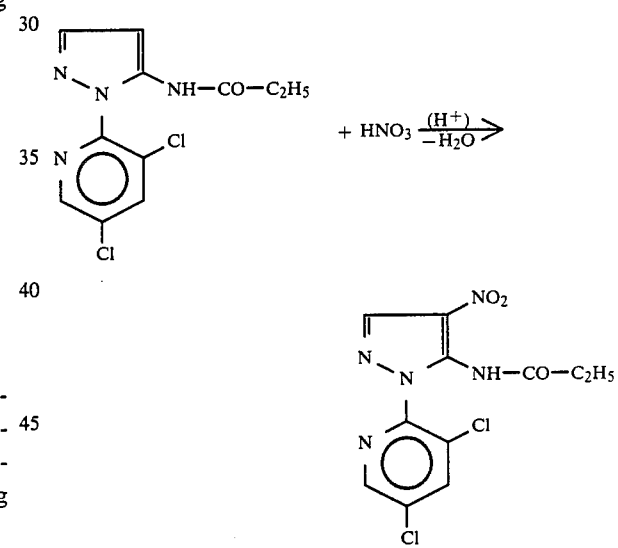

If, for example, 1-(3,5-dichloropyrid-2-yl)-4-nitro-5-propionamido-pyrazole is used as the starting substance, the course of the reaction in process (f) according to the invention can be represented by the following equation:

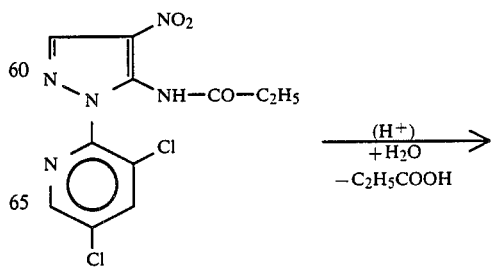

If, for example, 5-[N,N-bis(methanesulphon)-amido]-1-(3,5-dichloropyrid-2-yl)-pyrazole and ammonia are used as starting substances, the course of the reaction in process (g) according to the invention can be represented by the following equation:

If, for example, 5-amino-1-(3,5-dichloropyrid-2-yl)-pyrazole and methyl isocyanate are used as starting substances, the course of the reaction in process (h) according to the invention can be represented by the following equation:

If, for example, 5-bromo-4-nitro-1-(3,5-dichloropyrid-2-yl)-pyrazole and isopropylamine are used as starting substances, the course of the reaction in process (i) according to the invention can be represented by the following equation:

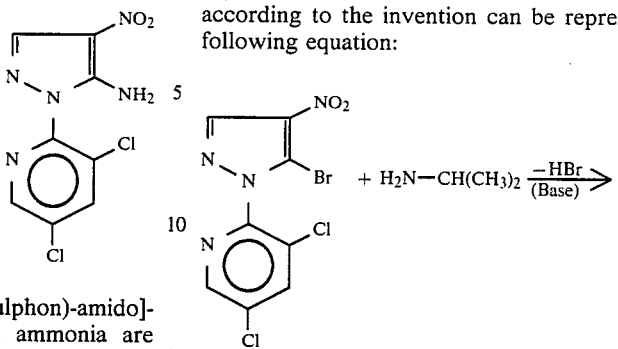

If, for example, 5-phenoxycarbonylamino-1-(3,5-dichloropyrid-2-yl)-pyrazole and methanol are used as starting substances, process (k) according to the invention can be represented by the following equation:

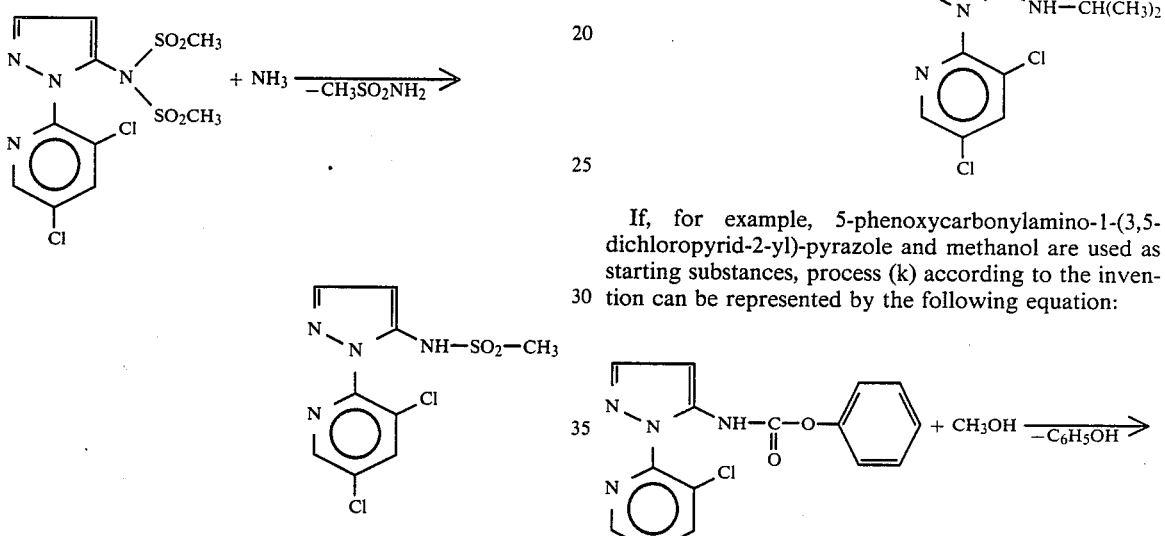

If, for example, 1-(3,5-dichloropyrid-2-yl)-5-methanesulphonamido-pyrazole and isopropylamine are used as starting substances, the course of the reaction in process (l) according to the invention can be represented by the following equation:

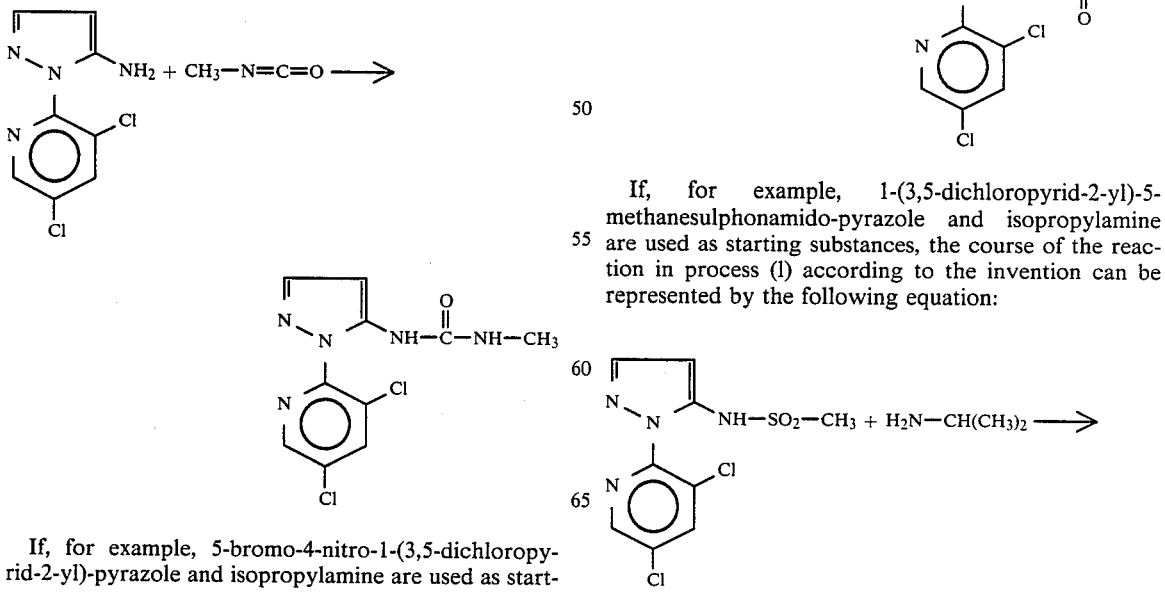

-continued

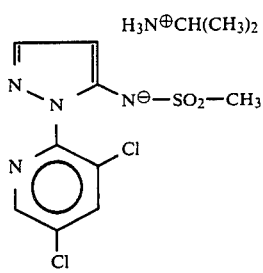

Formula (II) provides a general definition of the pyridylhydrazines required as starting substances for carrying out process (a) according to the invention. In this formula (II), Py preferably represents those radicals which have already been mentioned as preferred for this substituent in connection with the description of the substances of the formula (I) according to the invention.

The pyridylhydrazines of the formula (II) are known (compare, for example, U.S. Pat. No. 4,127,575; U.S. Pat. No. 3,609,158; DE-OS (German Published Specification) 2,558,399; and J. Chem. Soc. C., 1971, 167–174), or they can be prepared by processes which are known in principle, in a simple analogous manner, for example by a procedure in which halogenopyridines of the formula (XII)

$$\text{Py—Hal} \quad \text{(XII)}$$

in which
Py has the abovementioned meaning and
Hal represents halogen, in particular fluorine, chlorine or bromine,
are reacted with hydrazine hydrate, if appropriate in the presence of a diluent, such as, for example, pyridine or dioxane, at temperatures between 0° C. and 150° C., or in which, for example, aminopyridines of the formula (XIII)

$$\text{Py—NH}_2 \quad \text{(XIII)}$$

in which
Py has the abovementioned meaning,
are diazotized in a known manner, for example with sodium nitrite in the presence of an acid, such as, for example, sulphuric acid, and the diazonium salts thus obtainable are then reduced, likewise in a known manner, for example with tin-II chloride in the presence of an acid, such as, for example, hydrochloric acid, at temperatures between −20° C. and +80° C.

Formula (III) provides a general definition of the acrylonitrile derivatives furthermore required as starting substances for carrying out process (a) according to the invention. In this formula (III), $R^1$ and $R^2$ preferably represent those radicals which have already been mentioned as preferred for $R^1$ and $R^2$ in connection with the description of the substances of the formula (I) according to the invention. A preferably represents chlorine, bromine, hydroxyl, methoxy, ethoxy or dimethylamino.

The acrylonitrile derivatives of the formula (III) are known (compare DE-OS (German Published Specification) 3,129,429, DE-OS (German Published Specification) 3,206,878 and European Pat. No. 34,945; J. Chem. Soc. D 1255; 1970, Can. J. Chem. 48, 2104–2109 (1970); J. Heterocyclic Chem. 19, 1267–1273 (1982); and Can. J. Chem. 51, 1239–1244 (1973)), or they can be obtained by known processes, in a simple analogous manner.

The halogenopyridines of the formula (XII) and the aminopyridines of the formula (XIII) are generally known compounds of organic chemistry.

Formula (Ir) provides a general definition of the 4-alkoxycarbonyl-5-amino-pyrazoles required as starting substances for carrying out process (b) according to the invention. In formula (Ir), $R^1$ and Py preferbly represent those radicals which have already been mentioned as preferred for these substituents in connection with the description of the substances of the formula (I) according to the invention. $R^8$ preferably represents straight-chain or branched alkyl with 1 to 4 carbon atoms, in particular methyl or ethyl.

The 4-alkoxycarbonyl-5-amino-pyrazoles of the formula (Ir) are compounds according to the invention and are obtainable with the aid of process (a) according to the invention.

Formula (Ib) provides a general definition of the 5-amino-1-pyridyl-pyrazole derivatives required as starting substances for carrying out process (c) according to the invention. In this formula (Ib), $R^1$ and Py preferably represent those radicals which have already been mentioned as preferred for these substituents in connection with the description of the substances of the formula (I) according to the invention.

The 5-amino-1-pyridyl-pyrazole derivatives of the formula (Ib) are compounds according to the invention and are obtainable with the aid of process (b) according to the invention.

Formula (Is) provides a general definition of the 5-amino-1-pyridyl-pyrazoles required as starting substances for carrying out process (d) according to the invention. In this formula (Is), $R^1$, $R^2$, $R^3$ and Py preferably represent those radicals which have already been mentioned as preferred for these substituents in connection with the description of the substances of the formula (I) according to the invention.

The 5-amino-1-pyridyl-pyrazoles of the formula (Is) are compounds according to the invention.

5-Amino-1-pyridyl-pyrazoles of the formula (Is) in which $R^3$ represents hydrogen are obtainable with the aid of processes (a), (b), (c), (e) or (f) according to the invention. 5-Amino-1-pyridyl-pyrazoles of the formula (Is) in which $R^3$ is other than hydrogen are obtainable with the aid of processes (e), (f), (g) or (h) according to the invention.

5-Amino-1-pyridyl-pyrazoles of the formula (Id), which are prepared, for example, by process (d-α) according to the invention, can also be employed as starting substances in process (d-γ) according to the invention.

If mono-alkylated, -acylated, -sulphenylated, -sulphinylated or -sulphonylated compounds obtained with the aid of processes (d-α), (d-β) or (d-γ) according to the invention are reacted again by one of these processes, the corresponding disubstituted compounds are obtained.

Formula (V), (Va) and (Vb) provide general definitions of the compounds furthermore required for carrying out process (d) according to the invention. In formulae (V), (Va) and (Vb), $R^8$ preferably represents straight-chain or branched alkyl with 1 to 6 carbon atoms and $R^6$, $R^7$, X and n preferably represent those radicals which have already been mentioned as preferred for these substituents in connection with the description of the substances of the formula (I) according to the invention, $A^1$ preferably represents chlorine or bromine or represents a radical

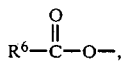

$A^2$ preferably represents chlorine or bromine and $A^3$ preferably represents chlorine, bromine, iodine, p-toluenesulphonyloxy or methoxysulphonyloxy.

The compounds of the formulae (V), (Va) and (Vb) are generally known compounds of organic chemistry.

Formula (It) provides a general definition of the 5-amino-1-pyridyl-pyrazoles required as starting substances for carrying out process (e) according to the invention. In this formula (It), $R^1$, $R^3$, $R^4$ and Py preferably represent those radicals which have already been mentioned as preferred for these substituents in connection with the description of the substances of the formula (I) according to the invention.

The 5-amino-1-pyridyl-pyrazoles of the formula (It) are compounds according to the invention and are obtainable with the aid of processes (a), (c), (d), (g), (i) or (k) according to the invention.

Formula (VI) provides a general definition of the electrophilic agents furthermore required as starting substances for carrying out process (e) according to the invention. In this formula (VI), $R^{2-1}$ preferably represents chlorine, bromine, nitroso or nitro, or represents formyl or alkanoyl with 1 to 6 carbon atoms in the alkyl part, or represents benzoyl which is optionally mono-substituted or polysubstituted by identical or different substituents, possible substituents being: halogen, in particular fluorine, chlorine and bromine, and in each case straight-chain or branched alkyl and alkoxy with in each case 1 to 4 carbon atoms, in particular methyl and methoxy, and halogenoalkyl with 1 to 4 carbon atoms and 1 to 9 identical or different halogen atoms, in particular trifluoromethyl.

$A^4$ preferably represents halogen, in particular chlorine or bromine, or represents hydroxyl, or represents alkyl- or aryl-sulphonyloxy, or represents alkanoyloxy or aroyloxy. Electrophilic reagents which can furthermore be used are sulphuryl chloride, phosphorus oxychloride/dimethylformamide, nitrating acid and other substances which can usually be employed for electrophilic substitution reactions.

The electrophilic agents of the formula (VI), like the other customary electrophilic reagents, are generally known compounds.

Formula (Iu) provides a general definition of the 5-acylamino-1-pyridyl-pyrazoles required as starting substances for carrying out process (f) according to the invention. In this formula (Iu), $R^1$, $R^6$ and Py preferably represent those radicals which have already been mentioned as preferred for these substituents in connection with the description of the substances of the formula (I) according to the invention.

$R^{2-2}$ preferably represents nitro, nitroso, fluorine, chlorine, bromine or iodine and $R_{4-2}$ preferably represents hydrogen, or represents straight-chain or branched alkyl with 1 to 4 carbon atoms, in particular methyl or ethyl.

The 5-acylamino-1-pyridyl-pyrazoles of the formula (Iu) are compounds according to the invention and are obtainable with the aid of processes (d) or (e) according to the invention.

Formula (Iv) provides a general definition of the 5-bis-sulphonyl-amino-pyrazoles required as starting substances for carrying out process (g) according to the invention. In this formula (Iv), $R^1$, $R^7$ and Py preferably represent those radicals which have already been mentioned as preferred for these substituents in connection with the description of the substances of the formula (I) according to the invention.

The 5-bis-sulphonyl-amino-pyrazoles of the formula (Iv) are compounds according to the invention and are obtainable with the aid of process (d) according to the invention.

Formula (Is) provides a general definition of the 5-amino-1-pyridyl-pyrazoles required as starting substances for carrying out process (h) according to the invention. In this formula (Is), $R^1$, $R^2$, $R^3$ and Py preferably represent those meanings which have already been mentioned as preferred for these substituents in connection with the description of the substances of the formula (I) according to the invention.

The 5-amino-1-pyridyl-pyrazoles of the formula (Is) are compounds according to the invention. Compounds of the formula (Is) in which $R^3$ represents hydrogen are obtainable with the aid of processes (a), (b), (c), (e) or (f) according to the invention.

Compounds of the formula (Is) in which $R^3$ is other than hydrogen are obtainable with the aid of processes (d), (e), (f), (g) or (h) according to the invention.

Formula (VII) provides a general definition of the iso(thio)cyanates furthermore required as starting substances for carrying out process (h) according to the invention. In this formula (VII), X represents oxygen or sulphur and $R^{4-3}$ preferably represents straight-chain or branched alkyl with 1 to 4 carbon atoms, or represents phenyl which is optionally mono-, di- or trisubstituted by identical or different substituents, possible substituents being: halogen and in each case straight-chain or branched alkyl and alkoxy with in each case 1 to 4 carbon atoms and halogenoalkyl with 1 to 4 carbon atoms and 1 to 9 identical or different halogen atoms. $R^{4-3}$ particularly represents methyl or ethyl, or represents phenyl which is optionally mono-, di- or trisubstituted by identical or different substituents from the group comprising fluorine, chlorine, methyl, methoxy and trifluoromethyl.

The iso(thio)cyanates of the formula (VII) are generally known compounds of organic chemistry.

Formula (VIII) provides a general definition of the 5-halogenopyrazoles required as starting substances for carrying out process (i) according to the invention. In this formula (VIII), $R^1$, $R^2$ and Py preferably represent those radicals which have already been mentioned as preferred for these substituents in connection with the description of the substances of the formula (I) according to the invention, and Y preferably represents chlorine or bromine.

The 5-halogeno-pyrazoles of the formula (VIII), are known in some cases (compare, for example, J. Heterocycl. Chem. 18, 9–14 (1981). Compounds which are not yet known are 5-halogeno-pyrazoles of the formula (VIIIa)

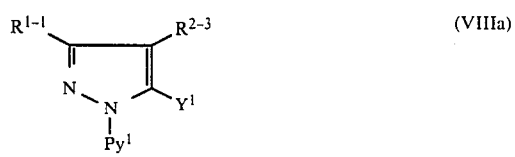

in which
R$^{1-1}$, R$^{2-3}$, Y$^1$ and Py$^1$ represent the same radicals as the corresponding radicals R$^1$, R$^2$, Y and Py in the analogous formula (VIII), but in the case where, at the same time, R$^{1-1}$ represents methyl, R$^{2-3}$ represents hydrogen and Y$^1$ represents chlorine, Py$^1$ does not represent the 5-nitro-2-pyridyl radical.

The 5-halogeno-pyrazoles of the formula (VIIIa), which are not yet known, are obtained, for example, by a process in which alkoxymethylenemalonic acid esters of the formula (XIV)

$$R^{11}-O-C=C \begin{array}{c} R^{1-1} \\ | \\ \end{array} \begin{array}{c} COOR^{10} \\ \diagdown \\ COOR^{10} \end{array} \qquad (XIV)$$

in which
R$^{1-1}$ has the abovementioned meaning and
R$^{10}$ and R$^{11}$ independently of one another in each case represent alkyl, in particular methyl or ethyl,
are initially reacted, in a first stage, with pyridylhydrazines of the formula (IIa)

Py$^1$—NH—NH$_2$ in which
Py$^1$ has the abovementioned meaning,
if appropriate in the presence of a diluent, such as, for example, methanol or ethanol, at temperatures between +10° C. and +80° C., and the pyrazolecarboxylic acid esters thus obtainable, of the formula (XV)

(XV)

in which
R$^{1-1}$, R$^{10}$ and Py$^1$ have the abovementioned meaning, are decarboxylated in a 2nd stage, if appropriate in the presence of a diluent, such as, for example, methanol, and if appropriate in the presence of a base, such as, for example, sodium hydroxide, at temperatures between +30° C. and +70° C. to give pyrazolinones of the formula (XVI)

(XVI)

in which
R$^{1-1}$ and Py$^1$ have the abovementioned meaning,
and these are reacted in a 3rd stage with halogenating agents, such as, for example, phosphorus oxychloride or phosphorus oxybromide, by customary known processes (compare, for example, Ber. dtsch. chem. Ges. 28, 35 (1895) or Liebigs Ann. Chem. 373, 129 (1910)), and, if appropriate, the 5-halogeno-pyrazoles thus obtainable, of the formula (VIIIb)

(VIIIb)

in which
R$^{1-1}$, Y$^1$ and Py$^1$ have the abovementioned meaning, are substituted in the 4-position in a 4th stage, in the generally customary manner, with electrophilic agents of the formula (VI)

R$^{2-1}$—A$^4$ (VI)

in which
R$^{2-1}$ represents halogen, nitroso, nitro, formyl, alkanoyl or aroyl and
A$^4$ represents an electron-withdrawing leaving group,
or with other customary electrophilic reagents, if appropriate in the presence of a diluent, such as, for example, glacial acetic acid, and if appropriate in the presence of a catalyst or reaction auxiliary, such as, for example, acetic anhydride, analogously to the procedure of process (e) according to the invention.

The new intermediate products of the formula (VIIIa) can also be obtained by reacting the 5-amino-1-pyridylpyrazoles according to the invention of the formula (Ia-1)

(Ia-1)

in which
R$^{1-1}$, R$^{2-3}$ and Py$^1$ have the abovementioned meanings,
with haloform compounds, such as in particular bromoform, in a generally customary manner in the presence of a diazotization agent, such as for example tert.-butyl nitrite, at temperatures between +20° and +120° C. (cf. also the preparation examples).

The intermediate products of the formula (XIVa)

$$Py^1-NH-NH-C=C \begin{array}{c} R^{1-1} \\ | \\ \end{array} \begin{array}{c} COOR^{10} \\ \diagdown \\ COOR^{10} \end{array} \qquad (XIVa)$$

in which
R$^{1-1}$, R$^{10}$ and Py$^1$ have the abovementioned meaning, which occur in the reaction of alkoxymethylenemalonic acid esters of the formula (XIV) with pyridylhydrazines of the formula (IIa) can also be isolated, if appropriate, and cyclized in a separate reaction stage.

The cyclization to give the pyrazolecarboxylic acid esters of the formula (XV) and subsequent decarboxylation thereof can be carried out, if appropriate, in one reaction stage as a "one-pot process" (compare, for example, Liebigs Ann. Chem. 373, 142 (1910)).

The alkoxymethylenemalonic acid esters of the formula (XIV) are generally known compounds of organic chemistry.

Preferred 5-halogeno-pyrazoles of the formula (VIIIa) are those in which $R^{1-1}$, $R^{2-3}$ and $Py^1$ represent the corresponding radicals $R^1$, $R^2$ and Py which have already been mentioned as preferred for these substituents in connection with the description of the substances of the formula (I) according to the invention and $Y^1$ preferably represents chlorine or bromine, but in the case where, at the same time, $R^{1-1}$ represents methyl, $R^{2-3}$ represents hydrogen and $Y^1$ represents chlorine, Py does not represent the 5-nitro-2-pyridyl radical.

In formula (VIIIa), $R^{1-1}$, $R^{2-3}$ and $Py^1$ particularly preferably represent the corresponding radicals $R^1$, $R^2$ and Py which have already been mentioned as particularly preferred for these radicals in connection with the description of the substances of the formula (I) according to the invention and $Y^1$ particularly preferably represents chlorine or bromine, but in the case where, at the same time, $R^{1-1}$ represents methyl, $R^{2-3}$ represents hydrogen and $Y^1$ represents chlorine, $Py^1$ does not represent the 5-nitro-2-pyridyl radical.

Formula (IX) provides a general definition of the amines furthermore required as starting substances for carrying out process (i) according to the invention. In this formula (IX), $R^{4-4}$ preferably represents straight-chain or branched alkyl with 1 to 6 carbon atoms, in particular methyl, ethyl, n- or i-propyl or n-, i-, s- or t-butyl, and $R^{3-1}$ preferably represents hydrogen, or represents straight-chain or branched alkyl with 1 to 6 carbon atoms, in particular methyl, ethyl, n- or i-propyl or n-, i-, s- or t-butyl.

The amines of the formula (IX) are likewise generally known compounds of organic chemistry.

Formula (Iw) provides a general definition of the (bis)carbamates required as starting substances for carrying out process (k) according to the invention. In this formula (Iw), $R^1$, $R^2$ and Py preferably represent those radicals which have already been mentioned as preferred for these substituents in connection with the description of the substances of the formula (I) according to the invention, and $R^{3-1}$ represents a radical —CO—O—Ar, or represents hydrogen, Ar preferably representing phenyl.

The (bis)carbamates of the formula (Iw) are compounds according to the invention and are obtainable with the aid of processes (d) or (e) according to the invention.

Formula (X) provides a general definition of the compounds furthermore required as starting substances for carrying out process (k) according to the invention. In this formula (X), $R^{6-1}$ preferably represents in each case straight-chain or branched alkoxy, alkylthio, alkylamino or dialkylamino with in each case 1 to 4 carbon atoms in the individual alkyl parts, or represents phenoxy, phenylthio or phenylamino, in each case monosubstituted or polysubstituted by identical or different substituents, possible phenyl substituents in each case being: halogen and in each case straight-chain or branched alkyl and alkoxy with in each case 1 to 4 carbon atoms, halogenoalkyl with 1 to 4 carbon atoms and 1 to 9 identical or different halogen atoms, in particular methyl, methoxy, chlorine and trifluoromethyl. $R^{6-1}$ particularly represents methoxy, ethoxy, methylthio, phenylthio or dimethylamino.

The compounds of the formula (X) are generally known compounds of organic chemistry.

Formula (Ix) provides a general definition of the 5-sulphonamido-pyrazoles required as starting substances for carrying out process (l) according to the invention. In this formula (Ix), $R^1$, $R^2$, $R^7$ and Py preferably represent those radicals which have already been mentioned as preferred for these substituents in connection with the description of the substances of the formula (I) according to the invention.

The 5-sulphonamido-pyrazoles of the formula (IX) are compounds according to the invention and are obtainable with the aid of processes (d), (e) and (g) according to the invention.

Formula (XI) provides a general definition of the salts furthermore required as starting substances for carrying out process (l) according to the invention. Alkali metal, alkaline earth metal, ammonium or transition metal hydroxides, oxides, carbonates, bicarbonates or readily soluble chlorides, sulphates, phosphates or nitrates are preferably used, such as, for example, sodium potassium or calcium hydroxide, carbonate or bicarbonate, calcium chloride, barium chloride, copper sulphate, nickel chloride or cobalt nitrate, or alkylamines, such as triethylamine, isopropylamine, diisopropylamine or butylamine.

The salts of the formula (XI) are generally known compounds.

Possible diluents in carrying out preparation process (a) both for the 1st and for the 2nd reaction stage are inert organic solvents. Alcohols, such as methanol, ethanol, propanol, butanol, ethylene glycol or ethylene glycol monomethyl or monoethyl ether are preferably used.

Possible reaction auxiliaries for carrying out the 1st stage of preparation process (a) are organic or inorganic acids. Sulphuric acid or acetic acid is preferably used, if appropriate also in the presence of a buffer substance, such as, for example, sodium acetate.

The reaction temperatures can be varied within certain ranges in carrying out the 1st stage of preparation process (a). The reaction is in general carried out between $-30°$ C. and $+50°$ C., preferably between $-20°$ C. and $+20°$ C.

Possible acid-binding agents for carrying out the 2nd stage of preparation process (a) are all the inorganic and organic bases which can usually be employed. Alkali metal carbonates or bicarbonates, such as sodium carbonate, potassium carbonate or potassium bicarbonate, are preferably used.

Process (a) according to the invention can also be carried out directly in one reaction step without isolation of the intermediate products of the formula (IV).

The reaction temperatures can be varied within a substantial range in carrying out the 2nd stage of preparation process (a), as in the case of the one-stage reaction procedure. The reaction is in general carried out between $0°$ C. and $200°$ C., preferably between $+50°$ C. and $+150°$ C.

For carrying out preparation process (a), both in the one-stage and in the two-stage reaction procedure, in general 1 to 3 moles, preferably 1 to 1.5 moles, of acrylonitrile derivative of the formula (III) and, in the case of the two-stage process, if appropriate in the 1st stage 1 to 10 moles of reaction auxiliary and if appropriate in the 2nd stage 1 to 10 moles of acid-binding agent, are employed per mole of pyridylhydrazine of the formula (II).

The reaction products of the formula (Ia) are worked up and isolated by customary processes, for example by removal of the organic diluent, precipitation of the reaction product in water, filtration with suction and drying of the product thus obtained.

Possible diluents for carrying out preparation process (b) are inorganic or organic solvents. Polar solvents, in particular alcohols, such as, for example, methanol, ethanol or propanol, or mixtures thereof with water, are preferably used.

Possible catalysts for carrying out preparation process (b) are all the catalysts which are usually employed for such ester hydrolyses. Bases, such as, for example, sodium hydroxide, sodium alcoholate or sodium carbonate, or acids, such as, for example, hydrochloric acid, hydrobromic acid or sulphuric acid, are preferably used.

The reaction temperatures can be varied within a substantial range in carrying out process (b) according to the invention. The reaction is in general carried out at temperatures between 20° C. and 150° C., preferably at temperatures between 50° C. and 100° C.

For carrying out preparation process (b), in general 1 to 15 moles, preferably 1 to 2.5 moles, of acid or basic catalyst are employed per mole of 4-alkoxycarbonyl-5-amino-pyrazole of the formula (Ir) and the mixture is warmed at the required reaction temperature for several hours. The reaction products of the formula (Ib) are worked up, isolated and purified by customary processes.

Possible diluents for carrying out preparation process (c) are likewise inorganic or organic, preferably polar, solvents.

Alcohols, such as, for example, methanol, ethanol or propanol, or mixtures thereof with water, are particularly suitable.

Possible catalysts for carrying out preparation process (c) are, preferably, acids, in particular inorganic mineral acids, such as hydrochloric acid, hydrobromic acid or sulphuric acid.

The reaction temperatures can be varied within a substantial range in carrying out preparation process (c). The reaction is in general carried out between +50° C. and +200° C., preferably between +70° C. and +120° C.

In carrying out process (c) according to the invention, in general 1 to 30 moles, preferably 1 to 15 moles, of catalyst acid are employed per mole of 5-amino-1-pyridyl-pyrazole derivative of the formula (Ib) and the mixture is warmed at the required temperature for several hours. The reaction products of the formula (Ic) are worked up, isolated and purified by generally customary processes.

If an acid catalyst is used, it is also possible to carry out processes (b) (ester hydrolysis) and (c) (decarboxylation) according to the invention in one reaction step as a one-pot process. In this case also, the reaction is carried out and the reaction products are worked up and isolated by generally customary methods (compare also the preparation examples).

Possible diluents for carrying out process (d) according to the invention are inert organic solvents. Solvents which are preferably used are aliphatic, cyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene and dichlorobenzene, ethers, such as diethyl ether, diisopropyl ether, dioxane, tetrahydrofuran or ethylene glycol diethyl ether or dimethyl ether, ketones, such as acetone, butanone, methyl isopropyl ketone or methyl isobutyl ketone, esters, such as ethyl acetate, nitriles, such as acetonitrile or propionitrile, and amides, such as dimethylformamide, dimethylacetamide, N-methylpyrrolidone or hexamethylphosphoric acid triamide. If compounds of the formulae (V), (Va) or (Vb) are used in liquid form, it is also possible to employ these in a corresponding excess as the solvent.

Possible acid-binding agents for carrying out process (d) according to the invention are all the inorganic and organic bases which can usually be employed. Bases which are preferably used are alkali metal hydrides, hydroxides, amides, carbonates or bicarbonates, such as, for example, sodium hydride, sodamide, sodium hydroxide, sodium carbonate or sodium bicarbonate, or also tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out preparation process (d). The reaction is in general carried out between −20° C. and +150° C., preferably between 0° C. and +100° C.

For carrying out preparation process (d), in general 1 to 20 moles, preferably 1 to 15 moles, of compound of the formula (V), (Va) or (Vb) and, if appropriate, 1 to 3 moles, preferably 1 to 2 moles, of acid-binding agent are employed per mole of 5-amino-1-pyridyl-pyrazole of the formula (Is). The reaction is carried out and the reaction products of the formula (Id) are worked up and isolated in the generally customary manner.

Possible diluents for carrying out process (e) according to the invention are all the solvents which can usually be employed for such electrophilic substitutions. The acids or mixtures possible as reagents, such as, for example, sulphuric acid, nitric acid, sulphuryl chloride, phosphorus oxychloride/dimethylformamide or nitrating acid, are preferably simultaneously used as the diluent.

Where appropriate, inert organic solvents, such as, for example, glacial acetic acid or chlorinated hydrocarbons, such as methylene chloride, chloroform or carbon tetrachloride, are also possible diluents.

Possible catalysts or reaction auxiliaries for carrying out preparation process (e) are likewise the catalysts customary for such reactions; acid catalysts, such as, for example, sulphuric acid, iron-III chloride or other Lewis acids, or acetic anhydride are preferably used.

The reaction temperatures can be varied within a substantial range in carrying out preparation process (e). The reaction is in general carried out between −50° C. and +200° C., preferably between −20° and +150° C.

For carrying out preparation process (e), in general 1 to 10 moles, preferably 1 to 5 moles, of electrophilic agent of the formula (VI) and, if appropriate, 0.1 to 10 moles of catalyst or reaction auxiliary are employed per mole of 5-amino-1-pyridyl-pyrazole of the formula (It). The reaction is carried out and the reaction products of the formula (Ie) are worked up and isolated in the generally customary manner.

Possible diluents for carrying out process (f) according to the invention are inorganic or organic polar solvents. Alcohols, such as, for example, methanol, ethanol or propanol, or mixtures thereof with water, are preferably used.

Possible catalysts for carrying out preparation process (f) are, preferably, acids, in particular hydrochloric acid or sulphuric acid.

The reaction temperatures can be varied within a substantial range in carrying out preparation process (f). The reaction is in general carried out between +20° C. and +150° C., preferably between +50° C. and +120° C.

For carrying out preparation process (f), in general 1 to 20 moles, preferably 1 to 10 moles, of catalyst acid are employed per mole of 5-acylamino-1-pyridyl-pyrazole of the formula (Iu) and the mixture is warmed at the required reaction temperature for several hours. The reaction products of the formula (If) are worked up, isolated and purified by customary methods.

Possible diluents for carrying out process (g) according to the invention are polar organic solvents or mixtures thereof with water. Alcohols, such as methanol, ethanol or propanol, or mixtures thereof with water, are preferably used.

Possible basic participants in the reaction in carrying out process (g) according to the invention are all the customary inorganic or organic bases. Amines or ammonia solutions or alkali metal carbonates or bicarbonates, such as sodium or potassium carbonate or sodium bicarbonate, are preferably used.

The reaction temperatures can be varied within a substantial range in carrying out process (g) according to the invention. The reaction is in general carried out between 0° C. and 80° C., preferably between 20° C. and 40° C.

For carrying out process (g) according to the invention, in general 1 to 30 moles, preferably 1 to 15 moles, of base are employed per mole of 5-bis-sulphonyl-amino-pyrazole of the formula (Iv).

The reaction mixture is stirred in a suitable diluent until the starting substance is no longer detectable on a chromatographic check (30 minutes to 20 hours). The reaction products of the formula (Ig) are worked up by customary methods.

Possible diluents for carrying out process (h) according to the invention are inert organic solvents. The diluents mentioned in the case of process (d) are preferably used. If the compounds of the formula (VII) are used in liquid form, it is also possible to employ them, in an appropriate excess, as the diluent.

Possible reaction auxiliaries for carrying out process (h) according to the invention are tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out process (h). The reaction is in general carried out between −20° C. and +150° C., preferably between 0° C. and +100° C.

For carrying out preparation process (h), in general 1 to 20 moles, preferably 1 to 15 moles, of compound of the formula (VII) and, if appropriate, 1 to 3 moles, preferably 1 to 2 moles, of reaction auxiliary are employed per mole of 5-amino-1-pyridylpyrazole of the formula (Is). The reaction is carried out and the reaction products of the formula (Ih) are worked up and isolated in the generally customary manner.

Possible diluents for carrying out process (i) according to the invention are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

If appropriate, process (i) according to the invention can be carried out in the presence of a suitable acid-binding agent.

Possible acid-binding agents are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible for a corresponding excess of the amine of the formula (IX) employed as the reaction partner simultaneously to be used as the acid-binding agent.

The reaction temperatures can be varied within a substantial range in carrying out process (i) according to the invention. The reaction is in general carried out at temperatures between −20° C. and +200° C., preferably at temperatures between 0° C. and +150° C.

For carrying out process (i) according to the invention, in general 1 to 10 moles, preferably 1 to 5 moles, of amine of the formula (IX) are employed per mole of 5-halogeno-pyrazole of the formula (VIII). The reaction is carried out and the reaction products of the formula (Ii) are worked up and isolated by generally customary processes.

Possible diluents for carrying out process (k) according to the invention are inert organic solvents. Solvents which are preferably used are aliphatic or aromatic, optionally halogenated hydrocarbons, such as benzine, benzene, toluene, xylene, pentane, hexane, heptane, cyclohexane, petroleum ether, ligroin, methylene chloride, ethylene chloride, chloroform, carbon tetrachloride, chlorobenzene or dichlorobenzene, ethers, such as diethyl ether, diisopropyl ether, ethylene glycol dimethyl ether, tetrahydrofuran or dioxane, ketones, such as acetone, butanone, methyl isopropyl ketone or methyl isobutyl ketone, esters, such as ethyl acetate, nitriles, such as acetonitrile or propionitrile, amides, such as dimethylformamide, dimethylacetamide, N-methylpyrrolidone or hexamethylphosphoric acid triamide, or alcohols, such as methanol, ethanol or isopropanol.

However, it is also possible for the compounds of the formula (X) used as reaction components simultaneously to be employed in a corresponding excess as the diluent.

If appropriate, process (k) according to the invention can be carried out in the presence of a basic catalyst. Possible basic catalysts are all the customary inorganic or organic bases. The bases mentioned in the case of process (i) are preferably used.

The reaction temperatures can likewise be varied within a substantial range in process (k) according to the invention. The reaction is in general carried out between 0° C. and +200° C., preferably between +20° C. and +150° C.

For carrying out process (k) according to the invention, in general 1 to 20 moles, preferably 1 to 10 moles, of the compound of the formula (X) are employed per mole of (bis)carbamate of the formula (Iw), and the mixture is warmed at the required temperature for several hours. The reaction products of the formula (Ik) are worked up and isolated by customary processes.

Possible diluents for carrying out process (l) according to the invention are polar organic solvents, water or aqueous mixtures. Alcohols, such as, for example, methanol, ethanol or propanol, mixtures thereof with water or pure water are preferably used.

The reaction temperatures can likewise be varied within a substantial range in carrying out preparation process (l). The reaction is in general carried out between 0° C. and +80° C., preferably between +20° C. and +40° C.

For carrying out process (l) according to the invention, in general 1 to 10 moles, preferably 1 to 5 moles, of salt of the formula (XI) or of amine are employed per mole of 5-sulphonamido-pyrazole of the formula (Ix).

To prepare the sodium, potassium or ammonium salts, a compound of the formula (Ix) is reacted with sodium hydroxide, potassium hydroxide or ammonium hydroxide or an amine in aqueous solution or an organic solvent, such as acetone, methanol, ethanol or dimethylformamide, and the salts are isolated by filtration or by evaporation of the solution and, if appropriate, purified by recrystallization.

The calcium, barium, magnesium, manganese, copper, nickel, tin, iron or cobalt salts are prepared from the sodium salts by treatment with a corresponding inorganic metal salt, for example calcium chloride, barium chloride, copper sulphate, nickel chloride or cobalt nitrite. The calcium salts can also be prepared by treatment of a compound of the formula (Ix) with calcium hydroxide.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, PaspaLum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be employed with particularly good success here for selectively combating monocotyledon and dicotyledon weeds in monocotyledon and dicotyledon crops, such as, for example, wheat or cotton.

The intermediate products of the formula (VIII) also have a powerful herbicidal activity.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polar substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated alphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorilonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquor and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soy beans. Mixtures with N,N-dimethyl-N'-(3-trifluoromethylphenyl)-urea; N,N-dimethyl-N'-(3-chloro-4-methylphenyl)-urea; N,N-dimethyl-N'-(4-isopropylphenyl)-urea; 2,4-dichlorophenoxyacetic acid; 2,4-dichlorophenoxypropionic acid; (2-methyl-4-chlorophenoxy)-acetic acid; (4-chloro-2-methyl-phenoxy)-propionic acid; 2-benzyloxy-ethyl, trimethylsilylmethyl or 2,2-diethoxyethyl 2-[4-(3,5-dichloropyrid-2-yloxy)-phenoxy]-propionate; methyl 5-(2,4-dichlorophenoxy)-2-nitrobenzoate; 3,5-diiodo-4-hydroxy-benzonitrile; 2-chloro-N-<[(4-methoxy-6-methyl-1,3,5-triazin-2-yl)-amino]-carbonyl>-benzenesulphonamide, 4-ethylamino-2-t-butylamino-6-methylthio-s-triazine; N-methyl-2-(benzothiazol-2-yloxy)-acetamide; N-(1-ethylpropyl)-3,4-dimethyl-2,6-dinitroaniline; chloroacetic acid N-(methoxymethyl)-2,6-diethylanilide; 2-ethyl-6-methyl-N-(1-methyl-2-methoxyethyl)-chloroacetanilide; 2,6-dinitro-4-trifluoromethyl-N,N-dipropylaniline; ethyl 2-{4-[[3-chloro-5-(trifluoromethyl)-2-pyridinyl]-oxy]-phenoxy} propanoate or 2,3,3-trichloroallyl N,N-diisopropyl-thiocarbamate and other triazinones, are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

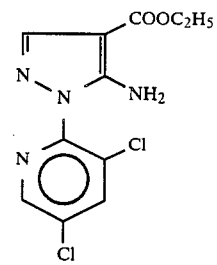

(Process (a)

16.9 g (0.1 mole) of ethyl ethoxymethylenecyanoacetate and 17.8 g (0.1 mole) of 3,5-dichloro-pyrid-2-ylhydrazine in 150 ml of ethoxyethanol are stirred at 80° C. for 5 hours and then at 120° C. for a further 2 hours. For working up, the solvent is removed in vacuo. 29.6 g (98% of theory) of 5-amino-1-(3,5-dichloro-pyrid-2-yl)-4-ethoxycarbonyl-pyrazole of melting point 98°–101° C. are obtained.

Example 2

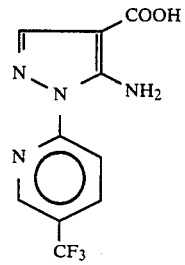

(Process (b)

10 ml of 45% strength aqueous sodium hydroxide solution are added to 18 g (0.06 mole) of 5-amino-1-(5-trifluoromethyl-pyrid-2-yl)-4-ethoxycarbonyl-pyrazole in 100 ml of 50% strength aqueous ethanol solution and the mixture is stirred at 80° C. for 4 hours. For working up, the solvent is removed in vacuo, the residue is taken up in 50 ml of water and the mixture is stirred into a solution of 20 ml of concentrated hydrochloric acid and 50 ml of water. The precipitate is filtered off with suction, washed with a little dilute hydrochloric acid and dried at 50° C. in vacuo. 15.4 g (94.4% of theory) of 5-amino-1-(5-trifluoromethyl-pyrid-2-yl)-pyrazole-4-carboxylic acid of melting point 196° C. (decomposition) are obtained.

Example 3

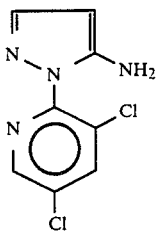

(Process (c))

16.5 g (0.06 mole) of 5-amino-1-(3,5-dichloropyrid-2-yl)-pyrazole-4-carboxylic acid are slowly heated to 80° C. in a mixture of 150 ml of water, 75 ml of concentrated hydrochloric acid and 20 ml of isopropanol and the reaction mixture is stirred at this temperature until the evolution of gas has ended. The clear solution formed is evaporated to dryness, the residue is suspended in methylene chloride, the suspension is neutralized with aqueous sodium carbonate solution, the organic phase is separated off and the aqueous phase is extracted twice more with methylene chloride. The combined organic phases are dried over sodium sulphate and freed from the solvent in vacuo. 12.7 g (92% of theory) of 5-amino-1-(3,5-dichloropyrid-2-yl)-pyrazole are obtained as an oil. $^1$H-NMR (CDCl$_3$/TMS as the internal standard): δ=4.55; 5.55; 7.43; 7.88; and 8.30 ppm.

Example 4

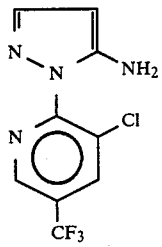

(Processes (b) and (c) as a "one-pot reaction")

10.5 g (0.03 mole) of 5-amino-1-(3-chloro-5-trifluoromethylpyrid-2-yl)-4-ethoxycarbonyl-pyrazole in 100 ml of aqueous 48% strength hydrobromic acid are slowly warmed to 80° C. The vigorous evolution of gas is suppressed by addition of 5 ml of isopropanol and the reaction mixture is slowly heated further to 115° C. to 120° C. After about 2 hours, the evolution of gas has ended. Stirring is continued at 115° C. to 120° C. for a further 3 hours, the hydrobromic acid is removed in vacuo, the residue is taken up in about 200 ml of methylene chloride and the mixture is neutralized with aqueous sodium bicarbonate solution. The organic phase is separated off and the aqueous phase is extracted twice more with methylene chloride; the combined organic phases are dried over magnesium sulphate and freed from the solvent in vacuo.

4.7 g (60% of theory) of 5-amino-1-(3-chloro-5-trifluoromethyl-pyrid-2-yl)pyrazole are obtained as an oil. $^1$H-NMR (CDCl$_3$/TMS): δ=4.1–5.0; 5.6; 7.5; and 8.1–8.6 ppm.

Example 5

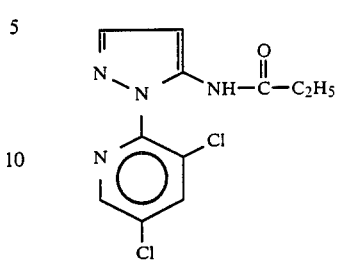

(Process (d))

4.3 ml (0.053 mole) of pyridine and 3.6 ml (0.051 mole) of propionyl chloride are successively added dropwise to 11 g (0.048 mole) of 5-amino-1-(3,5-dichloropyrid-2-yl)-pyrazole in 80 ml of methylene chloride at room temperature, with stirring. When the addition has ended, stirring is continued for a further 5 hours, the mixture is diluted with 70 ml of methylene chloride, washed successively with dilute hydrochloric acid, saturated sodium bicarbonate solution and sodium chloride solution and dried over magnesium sulphate and the solvent is removed in vacuo. 12.5 g (91.4% of theory) of 5-propionamido-1-(3,5-dichloropyrid-2-yl)-pyrazole of melting point 116°–124° C. are obtained.

Example 6

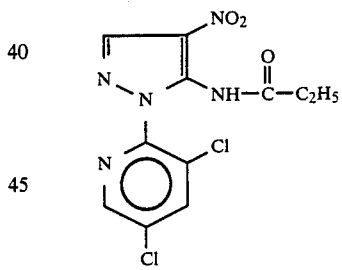

(Process (e))

1.5 ml (0.033 mole) of 98% strength nitric acid are added to 9.0 g (0.032 mole) of 5-propionamido-1-(3,5-dichloro-pyrid-2-yl)-pyrazole and 3.2 ml (0.035 mole) of acetic anhydride in 35 ml of glacial acetic acid at 10° C. and the mixture is stirred at room temperature for 6 hours. For working up, the mixture is concentrated in vacuo, the residue is taken up in 100 ml of methylene chloride and the mixture is neutralized with sodium bicarbonate solution, washed with sodium chloride solution, dried over magnesium sulphate and freed from the solvent in vacuo. 9.3 g (89% of theory) of 5-propionamido-1-(3,5-dichloropyrid-2-yl)-4-nitro-pyrazole of melting point 53° C.–56° C. are obtained.

Example 7

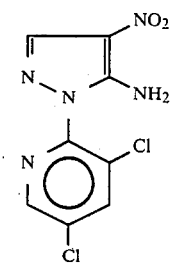

(Process f)

5 g (0.015 mole) of 5-propionamido-1-(3,5-dichloropyrid-2-yl)-4-nitro-pyrazole and 10 ml of concentrated hydrochloric acid are heated under reflux in 15 ml of ethanol for 4 hours, the solvent is distilled off in vacuo, the residue is taken up in 400 ml of methylene chloride and the mixture is neutralized with sodium bicarbonate solution, washed with sodium chloride solution, dried over sodium sulphate and freed from the solvent in vacuo. 3.8 g (92% of theory) of 5-amino-1-(3,5-dichloropyrid-2-yl)-4-nitropyrazole of melting point 194° C. are obtained.

The following 5-amino-1-pyridyl-pyrazoles of the general formula (I) are obtained in a corresponding manner and in accordance with the general statements on the preparation:

TABLE 2

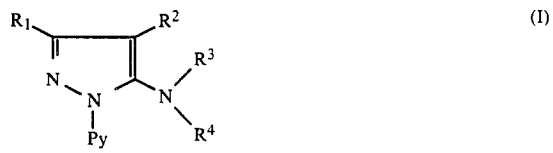

| Example No. | $R^1$ | $R^2$ | $R^3$ | $R^4$ | Py | Physical constants |
|---|---|---|---|---|---|---|
| 8 | H | $C_2H_5O-CO-$ | H | H | (pyridyl with $CF_3$) | 130–132° C. |
| 9 | H | $C_2H_5O-CO-$ | H | H | (pyridyl with $CF_3$ and Cl) | Melting point: 104–110° C. |
| 10 | H | HOOC | H | H | (pyridyl with Cl, Cl) | Melting point: 167° C. (decomposition) |
| 11 | H | H | H | H | (pyridyl with $CF_3$) | Melting point: 77–79° C. |
| 12 | H | H | $-CO-C_2H_5$ | H | (pyridyl with $CF_3$ and Cl) | Melting point: 80–82° C. |
| 13 | H | H | $-CO-C_2H_5$ | H | (pyridyl with $CF_3$) | Melting point: 110–114° C. |
| 14 | H | $NO_2$ | $-CO-C_2H_5$ | H | (pyridyl with $CF_3$) | Melting point: 128–130° C. |

TABLE 2-continued (I)

| Example No. | R¹ | R² | R³ | R⁴ | Py | Physical constants |
|---|---|---|---|---|---|---|
| 15 | H | NO$_2$ | —CO—C$_2$H$_5$ | H | 2-(3-Cl, 5-CF$_3$)pyridyl | Melting point: 114–118° C. |
| 16 | H | NO$_2$ | H | H | 2-(5-CF$_3$)pyridyl | Melting point: 114° C. |
| 17 | H | NO$_2$ | H | H | 2-(3-Cl, 5-CF$_3$)pyridyl | Melting point: 79–84° C. |
| 18 | H | H | —CO—CHCl$_2$ | H | 2-(3-Cl, 5-CF$_3$)pyridyl | Melting point: 79–84° C. |
| 19 | H | NO$_2$ | —CO—CHCl$_2$ | H | 2-(3-Cl, 5-CF$_3$)pyridyl | Melting point: 127–132° C. |
| 20 | H | H | —CO—CHCl$_2$ | H | 2-(3-Cl, 5-Cl)pyridyl | Melting point: 106° C. |
| 21 | H | NO$_2$ | —CO—CHCl$_2$ | H | 2-(3-Cl, 5-Cl)pyridyl | Melting point: 112° C. |

Example 22

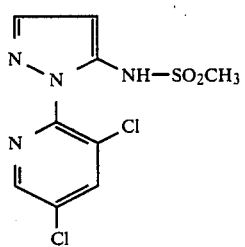

(Process d/variant β)

15 g (0.066 mol) of 5-amino-1-(3,5-dichloropyrid-2-yl)-pyrazole are dissolved in 65 ml of anhydrous pyridine and 9.2 ml (0.115 mol) of methanesulphonic acid chloride are added at 0° C.–5° C. over a period of 20 minutes. The reaction mixture is subsequently stirred for 1 hour and then discharged on to a mixture of methylene chloride and ice water. The organic phase is separated off, washed with dilute hydrochloric acid and freed from solvent in vacuo. The residue is dissolved in 200 ml of ethanol, 150 ml of concentrated aqueous ammonia is added and the mixture is stirred at room temperature for 18 hours. The ethanol is distilled off in vacuo, the residue is taken up in dichloromethane, washed with dilute hydrochloric acid and dried over magnesium sulphate and freed from the solvent in vacuo.

17.5 g (87% of theory) of 1-(3,5-dichloropyrid-2-yl)-5-methanesulphonamido-pyrazole with a melting point of 52°–54° C. are obtained.

Example 23

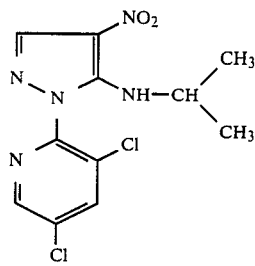

(Process i)

A mixture of 5.1 g (0.015 mol) of 1-(3,5-dichloropyrid-2-yl)-4-nitro-5-brompyrazole and 13.4 g (0.225 mol) of isopropylamine in 100 ml of methylene chloride is stirred at room temperature for 20 hours. The reaction mixture is evaporated in vacuo, the residue is taken up in 50 ml of methylene chloride and washed twice with 50 ml of water; the organic phase is dried over sodium sulphate and the solvent is distilled off in vacuo. The residue is crystallized by rubbing with petroleum ether, filtered off by suction and dried. 4.0 g (84.4% of theory) of 1-(3,5-dichloropyrid-2-yl)-4-nitro-5-isopropylaminopyrazole with a melting point of 123° C. are obtained.

PREPARATION OF THE STARTING PRODUCT

Example VIIIa-1

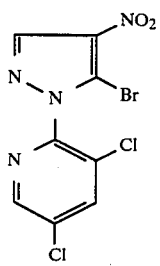

72 ml (0.96 mol) of tert.-butyl nitrite are added dropwise to 54.8 g (0.2 mol) of 1-(3,5-dichloropyrid-2-yl)-4-nitro-5-aminopyrazole in 250 ml (2.26 mol) of bromoform over a period of 30 minutes, the temperature of the reaction mixture rising to 80° C. during the dropwise addition. The mixture is stirred for a further 2 hours at 80° C. After cooling it is evaporated in vacuo. The residue is crystallized by rubbing with petroleum ether, filtered off by suction and dried.

64 g (94.7% of theory) of 1-(3,5-dichloropyrid-2-yl)-4-nitro-5-brompyrazole with a melting point of 122° C. are obtained.

Example 24

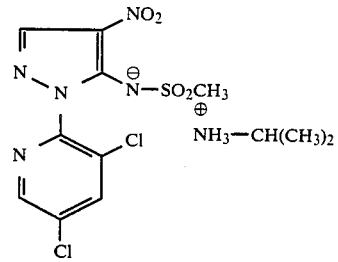

(Process 1)

2 g (5.7 mmol) of 1-(3,5-dichloropyrid-2-yl)-5-methanesulphonamido-4-nitropyrazole are suspended in 30 ml of anhydrous ethanol and 0.75 ml (8.5 mmol) of anhydrous isopropylamine are added. A clear solution is formed from which the solvent is distilled off in vacuo.

2.3 g (98.5% of theory) of 1-(3,5-dichloropyrid-2-yl)-5-methanesulphonamido-4-nitro-pyrazole isopropylammonium salt with a melting point of 99°–109° C. are obtained.

TABLE 2

| Example No. | $R^1$ | $R^2$ | $R^3$ | $R^4$ | Py | physical constant |
|---|---|---|---|---|---|---|
| 25 | H | $NO_2$ | H | $-(CH_2)_3CH_3$ | 3,5-dichloropyrid-2-yl | mp. 77° C. |
| 26 | H | $NO_2$ | $-SO_2-CH_3$ | H | 3,5-dichloropyrid-2-yl | mp. 85–123° C. |
| 27 | H | $NO_2$ | H | $-(CH_2)_2CH_3$ | 3,5-dichloropyrid-2-yl | mp. 87° C. |

USE EXAMPLES

The compound shown below was employed as the comparison substance in the use examples which follow:

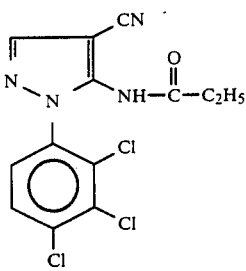

(A)

4-Cyano-5-propionamido-1-(2,3,4-trichlorophenyl)-pyrazole (known from DE-OS (German Published Specification) 3,226,513).

Example A

Pre-emergence test/Greenhouse

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clear superiority in useful plant selectivity in comparison with the prior art is shown, for example, by the compound according to preparation Examples 7, 19 and 27.

Example B

Post-emergence test/Greenhouse

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, a clear superiority in activity and in useful plant selectivity in comparison with the prior art is shown, for example, by the compound according to preparation Examples 7.

It is understood that the specification and examples are illustrative but not limitative of the present invention and that other embodiments within the spirit and scope of the invention will suggest themselves to those skilled in the art.

We claim:

1. A 5-amino-1-pyridyl-pyrazole of the formula

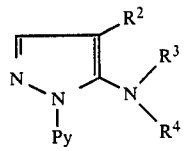

in which
R$^2$ represents hydrogen, nitro, nitroso, fluorine, chlorine, bromine or iodine, or represents a radical

wherein
R$^5$ represents hydrogen, hydroxyl or straight-chain or branched alkyl with 1 to 12 carbon atoms, or represents in each case straight-chain or branched alkenyl, alkinyl, alkoxyalkyl, alkylthioalkyl, alkoxy, alkylthio, alkylamino, dialkylamino or halogenoalkyl with in each case up to 4 carbon atoms in the individual alkyl parts and, in the case of halogenoalkyl, with up to 9 identical or different halogen atoms, or furthermore represents cycloalkyl which has 3 to 7 carbon atoms and is optionally monosubstituted or polysubstituted by identical or different substituents from the group consisting of halogen, C$_1$-C$_4$-alkyl and C$_1$-C$_4$-halogenoalkyl, or represents phenyl, phenoxy, phenylthio or phenylamino, in each case optionally monosubstituted or polysubstituted by identical or different substituents selected from the group consisting of halogen and in each case straight-chain or branched alkyl and alkoxy with in each case 1 to 4 carbon atoms and halogenoalkyl with 1 to 4 carbon atoms and 1 to 9 identical or different halogen atoms,
R$^3$ represents hydrogen, or represents a radical

or represents a radical —S(O)$_n$—R$^7$,
R$^4$ represents hydrogen, or represents a radical

or represents a radical —S(O)$_n$—R$^7$, or represents straight-chain or branched alkyl with 1 to 6 carbon atoms, or, in the case where R$^3$ represents a radical —SO$_2$—R$^7$, also represents one equivalent of an alkali, alkaline earth or transition metal cation bonded in salt form, or represents an optionally by C$_1$-C$_4$-alkyl or phenyl substituted ammonium ion, wherein R⁶ represents hydrogen, or represents straight-chain or branched alkyl with 1 to 12 carbon atoms, or represents in each case straight-chain or branched alkenyl or alkinyl with in each case 2 to 4 carbon atoms, or represents in each case straight-chain or branched alkoxyalkyl, alkylthioalkyl, alkoxy, alkylthio, alkylamino, dialkylamino or halogenoalkyl with in each case 1 to 4 carbon atoms in the individual alkyl parts and, in the case of halogenoalkyl, with 1 to 9 identical or different halogen atoms, or furthermore represents cycloalkyl which has 3 to 7 carbon atoms and is optionally monosubstituted or polysubstituted by identical or different substituents from the group consisting of halogen, $C_1$-$C_4$-alkyl and $C_1$-$C_4$-halogenoalkyl, or represents phenyl, phenoxy, phenylthio or phenylamino, in each case optionally monosubstituted or polysubstituted by identical or different substituents selected from the group consisting of halogen and in each case straight-chain or branched alkyl and alkoxy with in each case 1 to 4 carbon atoms and halogenoalkyl with 1 to 4 carbon atoms and 1 to 9 identical or different halogen atoms, X represents oxygen or sulphur, n represents the number 0, 1 or 2, R⁷ represents in each case straight-chain or branched alkyl or halogenoalkyl with in each case 1 to 4 carbon atoms and, where appropriate, 1 to 9 identical or different halogen atoms, or represents phenyl which is optionally monosubstituted or polysubstituted by identical or different substituents selected from the group consisting of halogen and in each case straight-chain or branched alkyl and alkoxy with in each case 1 to 4 carbon atoms and halogenoalkyl with 1 to 4 carbon atoms and 1 to 9 identical or different halogen atoms, and Py represents 2-pyridyl, 3-pyridyl or 4-pyridyl, in each case monosubstituted or polysubstituted by identical or different substituents selected from the group consisting of cyano, nitro, halogen, in each case straight-chain or branched alkyl, alkoxy and alkoxycarbonyl with in each case 1 to 4 carbon atoms in the alkyl part, in each case straight-chain or branched halogenoalkyl and halogenoalkoxy with in each case 1 to 4 carbon atoms and 1 to 9 identical or different halogen atoms and a radical —S(O)$_m$—R⁹, wherein R⁹ represents amino, or represents in each case straight-chain or branched alkyl, alkylamino or dialkylamino with in each case 1 to 4 carbon atoms in the individual alkyl parts, or represents halogenoalkyl with 1 to 4 carbon atoms and with 1 to 9 identical or different halogen atoms and m represents the number 0, 1 or 2.

2. A 5-amino-1-pyridyl-pyrazole according to claim 1 in which

R² represents hydrogen, nitro, nitroso, fluorine, chlorine, bromine or iodine, or represents a radical

wherein

R⁵ represents hydrogen, hydroxyl, methyl, ethyl, n- or i-propyl, n-, i-, s- or t-butyl, n- or i-pentyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 2-chloropropyl or heptafluoro-n-propyl, or represents cyclopropyl, cyclopentyl or cyclohexyl, in each case optionally mono-, di-, tri- or tetrasubstituted by identical or different substituents from the group consisting of fluorine, chlorine, bromine, methyl and trifluoromethyl, or represents phenyl, phenoxy, phenylthio or phenylamino, in each case optionally mono-, di- or trisubstituted by identical or different substituents from the group consisting of methyl, methoxy, chlorine and trifluoromethyl, R³ represents hydrogen, or represents a radical

or represents a radical —S(O)$_n$—R⁷,

R⁴ represents hydrogen, or represents a radical

or represents a radical —S(O)$_n$—R⁷, or represents methyl, ethyl, n- or i-propyl or n-, i-, s- or t-butyl, or, in the case where R³ represents a radical —SO$_2$—R⁷, also represents one equivalent of a sodium, potassium, magnesium, calcium, barium, copper, zinc, manganese, tin, iron, cobalt or nickel ion bonded in salt form, or represents an ammonium ion which is optionally mono-, di- or trisubstituted by identical or different substituents from the group consisting of methyl, ethyl, n- and i-propyl, n-, i-, s- and t-butyl and phenyl, wherein R⁶ represents hydrogen, methyl, ethyl, n- or i-propyl, n-, i-, s- or t-butyl, n- or i-pentyl, n- or i-hexyl, n- or i-heptyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 3-chloropropyl or heptafluoro-n-propyl, or represents cyclopropyl, cyclopentyl or cyclohexyl, in each case optionally mono-, di-, tri- or tetrasubstituted by identical or different substituents from the group consisting of fluorine, chlorine, bromine, methyl and trifluoromethyl, or represents phenyl, phenoxy, phenylthio or phenylamino, in each case optionally mono-, di- or trisubstituted by identical or different substituents from the group consisting of methyl, methoxy, chlorine and trifluoromethyl, R⁷ represents methyl, ethyl, n- or i-propyl, n-, i-, s- or t-butyl, chloromethyl, dichloromethyl, trichloromethyl or trifluoromethyl, or represents phenyl which is optionally mono-, di- or trisubstituted by identical or different substituents from the group consisting of methyl, methoxy, chlorine and trifluoromethyl, and Py represents 2-pyridyl or 4-pyridyl, in each case mono-, di-, tri- or tetrasubstituted by identical or different substituents, selected from the group consisting of cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)$_m$—R$^9$, wherein
R$^9$ represents amino, methylamino, ethylamino, dimethylamino, diethylamino, fluorodichloromethyl, difluoromethyl, tetrafluorethyl, trifluorochloroethyl, trifluoromethyl, methyl or ethyl and
m represents the number 0, 1 or 2.

3. A compound according to claim 1, wherein such compound is 5-amino-1-(3,5-dichloropyrid-2-yl)-4-nitro-pyrazole of the formula

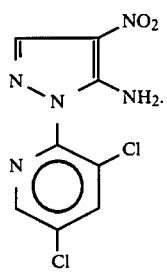

4. A compound according to claim 1, wherein such compound is 1-(3-chloro-5-trifluoromethyl-pyrid-2-yl)-4-nitro-5-dichloracetamido-pyrazole of the formula

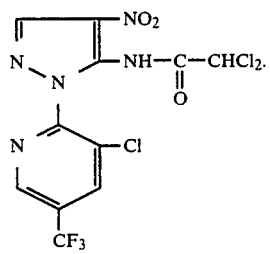

5. A compound according to claim 1, wherein such compound is 1-(3,5-dichloropyrid-2-yl)-4-nitro-5-n-propyl-amino-pyrazole of the formula

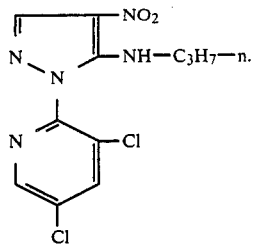

6. A herbicidal composition comprising a herbicidally effective amount of a compound according to claim 1 and a diluent.

7. A method of combating unwanted vegetation which comprises applying to such vegetation or to a locus from which it is desired to exclude such vegetation a herbicidally effective amount of a compound according to claim 1.

8. The method according to claim 1, wherein such compound is
5-amino-1-(3,5-dichloropyrid-2-yl)-4-nitro-pyrazole,
1-(3-chloro-5-trifluoromethyl-pyrid-2-yl)-4-nitro-5-dichloractamido-pyrazole or
1-(3,5-dichloropyrid-2-yl)-4-nitro-5-n-propyl-aminopyrazole.

9. A 5-halogenopyrazole of the formula

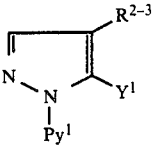

wherein
R$^{2-3}$ represents hydrogen, nitro, nitroso or halogen, or represents a radical

wherein
R$^5$ represents hydrogen, hydroxyl, alkyl, alkenyl, alkinyl, halogenoalkyl, alkoxyalkyl or alkylthioalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
Y$^1$ represents halogen and
Py$^1$ represents substituted C-linked pyridyl.

* * * * *

UNITED STATES PATENT AND TRADEMARK OFFICE
CERTIFICATE OF CORRECTION

PATENT NO. : 4,772,312
DATED : September 20, 1988
INVENTOR(S) : Otto Schallner, et al It is certified that error appears in the above-identified patent and that said Letters Patent is hereby corrected as shown below:

| | |
|---|---|
| Col. 3, line 51 | After "appropriate" insert --in-- |
| Col. 4, line 53 | Delete left side of formula and substitute  |
| Col. 6, line 26 | After "nitro" delete "and" and substitute --or-- |
| Col. 11, line 13 | After "formula (I)" insert --are those-- |
| Col. 20, line 26 | Delete "substance," and substitute --substances,-- |
| Col. 25, line 59 | Delete "$R_{4-2}$" and substitute --$R^{4-2}$-- |
| Col. 35, line 53 | Correct spelling of --Convolvulus-- |
| Col. 35, lines 66-67 | Correct --Paspalum-- |
| Col. 38, line 31 | After "2-yl" insert -- - -- |
| Col. 52, lines 41-57 | Delete "or represents a radical..... or represents optionally substituted arylamino," |

Signed and Sealed this

Eleventh Day of July, 1989

Attest:

DONALD J. QUIGG

Attesting Officer

Commissioner of Patents and Trademarks